United States Patent [19]

O'Lenick, Jr.

[11] Patent Number: 5,247,111

[45] Date of Patent: Sep. 21, 1993

[54] SILICONE ALKANOLAMIDES

[75] Inventor: Anthony J. O'Lenick, Jr., Lilburn, Ga.

[73] Assignee: Siltech Corporation, Toronto, Canada

[21] Appl. No.: 970,015

[22] Filed: Nov. 2, 1992

[51] Int. Cl.$^5$ .............................................. C07F 7/10
[52] U.S. Cl. ...................................... 556/420; 554/36; 554/39
[58] Field of Search ...................... 556/420; 554/39, 36

[56] References Cited

U.S. PATENT DOCUMENTS 3,658,864  4/1972  Golitz et al. ......................... 556/420
3,816,359  6/1974  Creamer ........................ 556/420 X
3,906,018  9/1975  Ostrozynski ........................ 556/420
4,104,296  8/1978  Pike ............................... 260/448.2 N
4,724,248  2/1988  Dexter et al. .................... 556/420 X
4,844,888  7/1989  Zawadzki ............................... 429/69

Primary Examiner—Paul F. Shaver

[57] ABSTRACT

The invention relates to a series of novel silicone alkanolamides a process or their preparation and the application of these materials in textile and personal care applications. This class of compounds are prepared by the reaction of a orboxy silicone and an alkanolamine. The products provide unique solubility in many organic solvents as well as being very substantive to hair skin and fiber. The compounds are useful or conditioning hair, skin and fiber and are particularity useful in personal care products like two in one shampoos.

18 Claims, No Drawings

SILICONE ALKANOLAMIDES

BACKGROUND OF THE INVENTION

1. Field of the Invention

The present invention relates to a series of novel silicone alkanolamides, a process or their preparation and the application of these materials as conditioners and softeners for hair, skin and textile fibers. The compounds of the present invention are prepared by reacting a an alkanoalamine with a carboxy containing silicone.

2. Arts and Practices

Silicone compounds have been known to be active at the surface of cellulose and synthetic fibers as well as paper. They are good nondurable lubricants and are very stable to oxidation, however, their high cost and lack of efficiency at low concentrations as well as low durability have made their acceptance in commercial products quite low.

In addition to their high cost, silicone compounds have little or no solubility in mineral oils, fatty triglycerides and other classical fatty quaternary compounds used for softening. This has resulted in the inability to prepare stable blends for use as a textile fiber treatment.

In many applications, there is a desire for a more fatty soluble softener. The desired molecule should have the desirable softening and antistatic properties of silicone, yet have compatibility with traditional fatty materials and oils. Even though a textile softener which has both the desirable softening and antistatic properties of silicone as well as compatibility with fatty compounds has been a long felt need, it isn't until the compounds of the present invention that such a system has been attained.

Carboxy containing silicone compounds useful as raw materials in the practice of the present invention are known to those skilled in the art. U.S. Pat. No. 4,844,888 issued in 1989 to Zawadizki discloses the carboxy containing silicone compounds useful as raw materials in the preparation of the compounds of the present invention.

U.S. Pat. No. 4,104,296 issued in 1978 to Pike teaches that butyrolactone can be reacted with an amino silane or siloxane.

THE INVENTION

Object of the Invention

It is the object of the present invention to provide novel silicone alkanolamides. These compounds are substantive to the surface of a fiber and other textile materials including cellulosic material and have increased solubility in fatty materials including mineral oil, fatty triglycerides and traditional fatty quaternary ammonium compounds. The compounds of the present invention render the lubricity, and hydrophobicity generally seen in silicone compounds, but because they contain an amido group they have greater solubility in hydrocarbon oils as well as fatty materials than the traditional silicone compounds which are insoluble in those materials.

It is another objective of the current invention to provide a novel recess for the preparation of silicone alkanolamides. It is still another objective of the invention to provide silicone alkanolamides which can be used in personal care, textile, and industrial formulations to render softness and lubrication to the substrates being treated. The superior solubility properties are an important benefit, since this is a major aspect of consumer perception of softness in consumer and industrial laundry applications. Application of the compounds of the invention can be from solvent, aqueous dispersion or solution, or applied neat 1n these processes.

SUMMARY OF THE INVENTION

The present invention relates to novel silicone alkanolamides. These compounds by virtue of the amide group are soluble in fatty and hydrocarbon products, but have many of the functional softening and lubrication properties of silicone. These materials are excellent additives for highly effective surface modifying finishes for fiber and textiles. The compounds of the present invention are substantive to cellulosic and synthetic fibers as well as metal surfaces and plastic polymers.

As will become clear from the disclosure, the compounds of the present invention while having silicone present in the molecule, have unique solubility in organic materials like triglycerides, mineral oil and the like. This property is a direct result of the structure. The pendant group needs to contain (a) a silicone atom linked covalently through carbon to (b) a amide group.

The compounds of the present invention conform to the following structure:

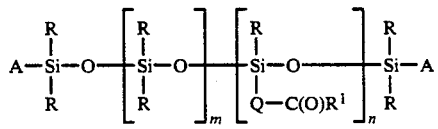

Wherein
R is methyl;
$R^1$ is

Q is a $-(CH_2)_c-$
c is an integer ranging from 3 to 17;
A is either $-R$ or $-Q-C(O)-R^1$.
m is an integer ranging from 1 to 200;
n is an integer ranging from 1 to 10;
a and b are each 0, 1 or 2 with the proviso that a+b be equal to 2.
$R^2$ is $-(CH_2-CH(R^4))-OH$:
$R^3$ is $-(CH_2-CH(R^4))-OH$ or H;
$R^4$ is H or $CH_3$.

These materials will allow for the solubilization in both fatty oils and silicone oils.

The compounds of the present invention are prepared by the reaction of a carboxy silicon with an alkanolamide. Suitable alkanolamines conform to the following structure:

a and b are each 0, 1 or 2 with the proviso that a+b be equal to 2.
$R^2$ is $-(CH_2-CH(R^4))-OH$;
$R^3$ is $-(CH_2-CH(R^4))-OH$ or H;
$R^4$ is H or $CH_3$.

The process used for the preparation of the compounds of the present invention comprises the amidification reaction of (a) a carboxy containing silicone compound conforming to the following structure:

$$A-\underset{R}{\overset{R}{Si}}-O-\left[\underset{R}{\overset{R}{Si}}-O\right]_m-\left[\underset{Q-C(O)OR'}{\overset{R}{Si}}-O\right]_n-\underset{R}{\overset{R}{Si}}-A$$

Wherein
R is methyl:
R is hydrogen:
Q is —(CH$_2$)$_c$;
c is an integer from 3 to 17;
A is selected from the group consisting of methyl and

—Q—C(O))R';

with
(b) an alkanolamine conforming to the following structure:

$$\underset{(R^3)b}{\overset{N-(R^2)a}{|}}$$

wherein;
a and b are each 0, 1 or 2 with the proviso that a+b be equal to 2.
R$^2$ is —(CH$_2$—CH(R$^4$))—OH;
R$^3$ is —(CH$_2$—CH(R$^4$))—OH or H;
R$^4$ is H or CH$_3$.
said amidification reaction to be carried out by mixing said carboxy silicone and said alkanolamine and heating said mixture to a temperature of between 120° and 250° C. for between 1 and 15 hours. Water is distilled off.

PREFERRED EMBODIMENTS

In a preferred embodiment, the temperature of the reaction ranges from 150° to 200° C.

In a still more preferred embodiment the temperature ranges from 150° to 180° C.

In a preferred embodiment the alkanolamine is diethanolamine.

In a preferred embodiment the alkanolamine is monoethanolamine.

In a preferred embodiment the alkanolamine is monoisopropanolamine.

In a preferred embodiment the alkanolamine is disiopropanolamine.

In a preferred embodiment the alkanolamine is diglycolamine.

EXAMPLES

The compounds of the present invention are prepared by the reaction of a carboxy silicone compound and an alkanolamine. Examples of suitable reactants are as follows:

REACTANTS

Alkanolamines

The various alkanolamines listed are all items of commerce and are prepared by methods known to those skilled in the art.

Example A Monoethanolamine H—N—CH$_2$CH$_2$OH
Example B Diethanolamine N—(CH$_2$CH$_2$OH)$_2$
Example C Monisopropanolamine H—N—CH$_2$CH(CH$_3$)OH
Example D Diisopropanolamine N—(CH$_2$CH(CH$_3$)OH)$_2$

Carboxy Silicone Compounds

Many manufacturers offer a series of carboxy functional silicone compounds suitable for use as raw materials in the preparation of the esters of the present invention. These materials are marketed under the many trade names. Siltech Inc. and Dow Corning.

The preferred method of placing this type of reactive carboxy group into the silicone polymer is by the reaction of silanic hydrogen containing polymer with a terminal unsaturated carboxylate. This technology is well known to those skilled in the art.

$$A-\underset{R}{\overset{R}{Si}}-O-\left[\underset{R}{\overset{R}{Si}}-O\right]_m-\left[\underset{Q-C(O)OR'}{\overset{R}{Si}}-O\right]_n-\underset{R}{\overset{R}{Si}}-A$$

Wherein
R is methyl:
R is hydrogen:
Q is —(CH$_2$)$_c$;
c is an integer from 3 to 17;
A is methyl;

| Example | Name | c | n | m |
|---|---|---|---|---|
| 1 | Siltech C 1000 | 10 | 3 | 15 |
| 2 | Siltech C 1100 | 10 | 1 | 20 |
| 3 | Siltech C 1200 | 3 | 4 | 50 |
| 4 | Siltech C 1300 | 3 | 2 | 200 |
| 5 | Siltech C 1400 | 4 | 1 | 29 |
| 6 | Siltech C 1500 | 17 | 3 | 1 |
| 7 | Siltech C 1600 | 17 | 4 | 150 |
| 8 | Siltech C 1700 | 4 | 10 | 55 |

Terminal Substituted Carboxy Silicones

Terminal substituted carboxy silicone compounds are well known and are marketed in the trade under many names.

The preferred method of placing this type of carboxyl group into the silicone polymer is by the reaction of terminal silanic hydrogen containing polymer with a terminal vinyl containing carboxy compound.

$$A-\underset{R}{\overset{R}{Si}}-O-\left[\underset{R}{\overset{R}{Si}}-O\right]_m-\left[\underset{Q-C(O)OR'}{\overset{R}{Si}}-O\right]_n-\underset{R}{\overset{R}{Si}}-A$$

Wherein
R is methyl;
R is hydrogen;
Q is (CH$_2$)$_c$;
c is an integer from 3 to 17;
n is 0;
A is —Q—C(O)OR'

| Example | Name | c | m |
|---|---|---|---|
| 9 | Siltech CT 701 | 10 | 1 |
| 10 | Siltech CT 706 | 3 | 200 |
| 11 | Siltech CT 710 | 17 | 50 |
| 12 | Siltech CT 750 | 10 | 100 |
| 13 | Siltech CT 790 | 3 | 150 |

General Reaction Conditions

The reaction can be run with either a stiochiometric amount of the alkanolamine, or an excess of the alkanolamine.

Into a suitable round bottom, three neck flask equipped with a thermometer and a nitrogen sparge is added the specified number of grams of the specified silicone compound and the specified number of grams of the specified alkanoalamine. The reaction mass is blanketed with nitrogen and heated to 150° -200° C. under the inert nitrogen blanket. Within our to five hours the acid value is vanishingly low. The product is a clear liquid and is used without additional purification.

Example 14

Into a suitable round bottom, three neck flask equipped with a thermometer and a nitrogen sparge is added 609.0 grams of silicone example 1 and 120.0 grams of Example A. The reaction mass is then blanketed with nitrogen and heated to 150°-200° C. This temperature is maintained for four to five hours. The acid value is vanishingly low after this period. The product is a clear liquid and is used without additional purification.

Examples 15-66

Example 14 is repeated only this time substituting the specified number of grams of the specified alkanolamine and the specified type and number of grams of silicone compound as shown below:

| Example | Alkanolamine Reactant Example | Grams | Silicone Compound Example | Grams |
|---|---|---|---|---|
| 15 | A | 60.0 | 1 | 609.0 |
| 16 | B | 105.0 | 1 | 609.0 |
| 17 | C | 74.0 | 1 | 609.0 |
| 18 | D | 133.0 | 1 | 609.0 |
| 19 | A | 60.0 | 2 | 1827.0 |
| 20 | B | 105.0 | 2 | 1827.0 |
| 21 | C | 74.0 | 2 | 1827.0 |
| 22 | D | 133.0 | 2 | 1827.0 |
| 23 | A | 60.0 | 3 | 1051.0 |
| 24 | B | 105.0 | 3 | 1051.0 |
| 25 | C | 74.0 | 3 | 1051.0 |
| 26 | D | 133.0 | 3 | 1051.0 |
| 27 | A | 60.0 | 4 | 7570.0 |
| 28 | B | 105.0 | 4 | 7570.0 |
| 29 | C | 74.0 | 4 | 7570.0 |
| 30 | D | 133.0 | 4 | 7570.0 |
| 31 | A | 60.0 | 5 | 2409.0 |
| 32 | B | 105.0 | 5 | 2409.0 |
| 33 | C | 74.0 | 5 | 2409.0 |
| 34 | D | 133.0 | 5 | 2409.0 |
| 35 | A | 60.0 | 6 | 361.0 |
| 36 | B | 105.0 | 6 | 361.0 |
| 37 | C | 74.0 | 6 | 361.0 |
| 38 | D | 133.0 | 6 | 361.0 |
| 39 | A | 60.0 | 7 | 3100.0 |
| 40 | B | 105.0 | 7 | 3100.0 |
| 41 | C | 74.0 | 7 | 3100.0 |
| 42 | D | 133.0 | 7 | 3100.0 |
| 43 | A | 60.0 | 8 | 524.2 |

-continued

| Example | Alkanolamine Reactant Example | Grams | Silicone Compound Example | Grams |
|---|---|---|---|---|
| 44 | B | 105.0 | 8 | 524.2 |
| 45 | C | 74.0 | 8 | 524.2 |
| 46 | D | 133.0 | 8 | 524.2 |
| 47 | A | 60.0 | 9 | 290.0 |
| 48 | B | 105.0 | 9 | 290.0 |
| 49 | C | 74.0 | 9 | 290.0 |
| 50 | D | 133.0 | 9 | 290.0 |
| 51 | A | 60.0 | 10 | 7553.0 |
| 52 | B | 105.0 | 10 | 7553.0 |
| 53 | C | 74.0 | 10 | 7553.0 |
| 54 | D | 133.0 | 10 | 7553.0 |
| 55 | A | 60.0 | 11 | 2200.0 |
| 56 | B | 105.0 | 11 | 2200.0 |
| 57 | C | 74.0 | 11 | 2200.0 |
| 58 | D | 133.0 | 11 | 2200.0 |
| 59 | A | 60.0 | 12 | 4000.0 |
| 60 | B | 105.0 | 12 | 4000.0 |
| 61 | C | 74.0 | 12 | 4000.0 |
| 62 | D | 133.0 | 12 | 4000.0 |
| 63 | A | 60.0 | 13 | 5700.0 |
| 64 | B | 105.0 | 13 | 5700.0 |
| 65 | C | 74.0 | 13 | 5700.0 |
| 66 | D | 133.0 | 13 | 5700.0 |

The compounds of the present in were found to provide outstanding softness and lubrication to fibers and hair.

What is claimed is:

1. A silicone alkanolamide which conforms to the following structure:

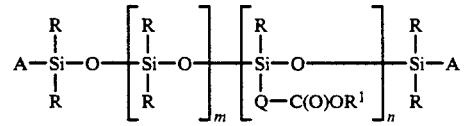

Wherein
R is methyl;
$R^1$ is $$\begin{array}{c} N-(R^2)_a \\ | \\ (R^3)_b \end{array}$$

Q is a $-(CH_2)_c-$
c is an integer ranging from 3 to 17;
A is either $-R$ or $-Q-C(O)-R^1$,
m is an integer ranging from 1 to 200;
n is an integer ranging from 1 to 10;
a and b are each 0, 1 or 2 with the proviso that a+b be equal to 2.
$R^2$ is $-(CH_2-CH(R^4))-OH$;
$R^3$ is $-(CH_2-CH(R^4))-OH$; or H;
$R^4$ is H or $CH_3$.

2. A compound of claim 1 wherein
R is methyl;
R is hydrogen;
Q is $(CH_2)_c$;
c is an integer from 3 to 17;
A is methyl, 3. A compound of claim 1 wherein
R is methyl;
R is hydrogen;
Q is $(CH_2)_c$;
c is an integer from 3 to 17;

n is 0;
A is —Q—C(O)OH.

4. A compound of claim 1 wherein

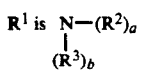

a is 1
b is 1
R² is —(CH₂—CH(R⁴))—OH;
R³ is H;
R⁴ is H.

5. A compound of claim 1 wherein

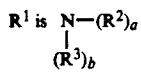

a is 1;
b is 1;
R² is —(CH₂—CH(R⁴))—OH;
R³ is —(CH₂—CH(R⁴))—OH;
R⁴ is H.

6. A compound of claim 1 wherein
R¹ is

a is 1;
b is 1;
R² is —(CH₂—CH(R⁴))—OH;
R³ is —H;
R⁴ is —CH₃.

7. A compound of claim 1 wherein
R¹ is

a is 1;
b is 1;
R² is —(CH₂—CH(R⁴))—OH;
R³ is —(CH₂—CH(R⁴))—OH;
R⁴ is —CH₃.

8. A process for the preparation of a silicone alkanolamide which comprises the amidification reaction of
(a) a carboxy containing silicone compound conforming to the following structure:

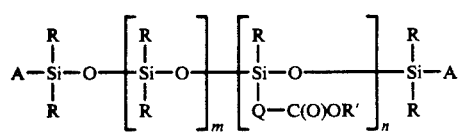

Wherein
R is methyl;
R' is hydrogen
Q is —(CH₂)c;
c is an integer from 3 to 17:
A is selected from the group consisting of methyl and

—Q—C(O))R';

m is an integer ranging from 1 to 200:

n is an integer ranging from 1 to 10;
with
(b) an alkanolamide conforming to the following structure:

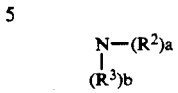

wherein:
a and b are each 0, 1 or 2 with the proviso that a+b be equal to 2.
R² is —(CH₂—CH(R⁴))—OH;
R³ is —(CH₂—CH(R⁴))—OH or H;
R⁴ is H or CH₃.
said amidification reaction to be carried out by mixing said carboxy silicone and said alkanolamine and heating said mixture to a temperature of between 120° and 250° C. for between 1 and 15 hours.

9. A process of claim 8 wherein said carboxy silicone conforms to the following structure:

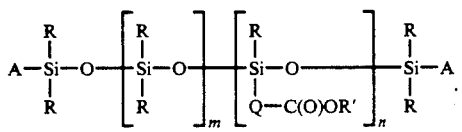

Wherein
R is methyl;
R' is hydrogen;
Q is —(CH₂)c;
c is an integer from 3 to 17;
A is methyl;
m is an integer ranging from 1 to 200;
n is an integer ranging from 1 to 10.

10. A process of claim 8 wherein said carboxy silicone conforms to the following structure;

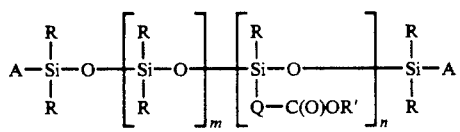

Wherein
R is methyl;
R' is hydrogen;
Q is —(CH₂)c;
c is an integer from 3 to 17;
n is 0;
m is an integer ranging from 1 to 200;
A is —Q—C(O)OR'.

11. A process of claim 9 wherein said alkanolamine is diethanolamine.

12. A process of claim 9 wherein said alkanolamine is monoethanolamine.

13. A process of claim 9 wherein said alkanolamine is monoisopropanolamine.

14. A process of claim 9 wherein said alkanolamine is diisopropanolamine.

15. A process of claim 10 wherein said alkanolamine is diethanolamine.

16. A process of claim 10 wherein said alkanolamine is monoethanolamine.

17. A process of claim 10 wherein said alkanolamine is monoisopropanolamine.

18. A process of claim 10 wherein said alkanolamine is diisopropanolamine.

* * * * *